United States Patent [19]

Freeman

[11] 4,304,225
[45] Dec. 8, 1981

[54] CONTROL SYSTEM FOR BODY ORGANS

[75] Inventor: Maynard L. Freeman, Hillside, Ill.

[73] Assignee: Lloyd and Associates, Chicago, Ill.

[21] Appl. No.: 34,224

[22] Filed: Apr. 30, 1979

[51] Int. Cl.$^3$ .............................................. A61H 7/00
[52] U.S. Cl. ....................................................... 128/60
[58] Field of Search ................... 128/1 D, 55, 63, 54, 128/58, 60, 62 R, 327, 686

[56] References Cited

U.S. PATENT DOCUMENTS

| 1,953,424 | 4/1934 | Miller | 128/63 |
| 3,955,563 | 5/1976 | Maione | 128/55 |

OTHER PUBLICATIONS

Kantrowitz et al. "Journal of the American Medical Association", vol. 203, No. 2, Jan. 8, 1968 pp. 135–140.
Moulepeulos et al. "American Heart Journal" vol. 63, 1962, pp. 669–675.
National Institutes of Health Publication No. 79-1670 Jul., 1979.
Department of Health Education & Welfare Publication No. (NIH) 78-1601.
Devices & Technology Branch Contractors Meeting 1979, U.S. Department of Health, 10–12 Dec. 1979.

*Primary Examiner*—William E. Kamm
*Attorney, Agent, or Firm*—Bernard L. Kleinke

[57] ABSTRACT

In a body organ control system having a pulse generator connected to a source of electrical power for generating a series of electrical timing pulses, an auxiliary pumping device is attached to a portion of the body organ for compressing and releasing it alternatingly in response to the series of timing pulses. The pumping device includes a compressor which has an opening therein for receiving and at least partially surrounding the body organ. The compressor is movable periodically to reduce substantially and forcibly the cross-sectional area of the opening by a predetermined amount to squeeze the surrounded portion of the body organ to force body materials therefrom. The pumping device includes an electrical force producing device, such as an electrical motor or a pump, which responds to the timing pulses for applying force to the compressor to cause it to reduce substantially the cross-sectional area of the opening against the force of the body organ being squeezed upon the occurrence of each one of the pulses and for releasing the compressor to permit the body organ to expand rapidly back to its unstressed normal size and shape during the time intervals between the pulses. In this manner, for example, the flow rate of a diseased heart of a person can be increased substantially, whereby the physical activities of such a person can be increased substantially.

9 Claims, 5 Drawing Figures

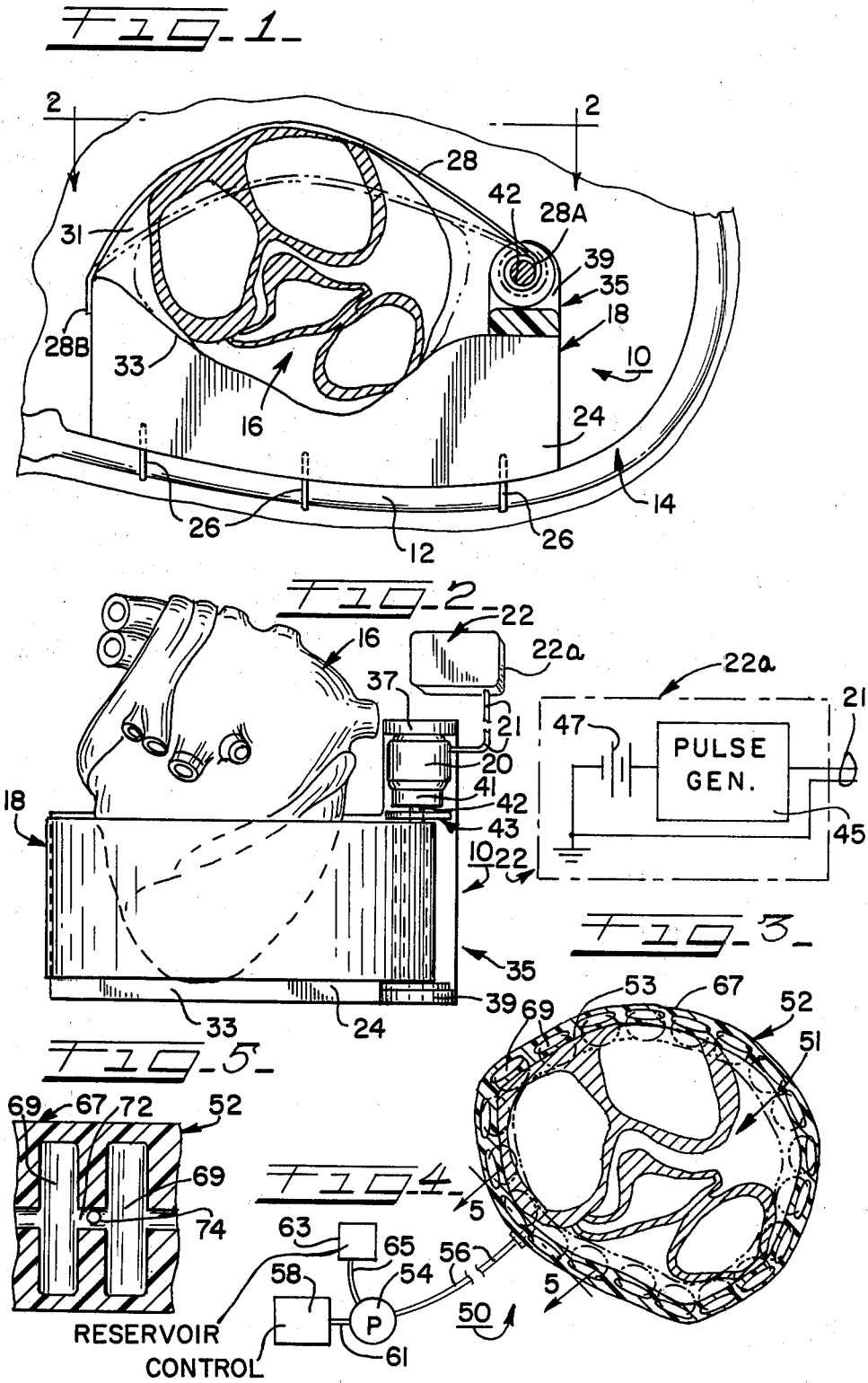

CONTROL SYSTEM FOR BODY ORGANS

BRIEF SUMMARY OF THE INVENTION

The present invention relates in general to a control system for body organs, and it more particularly relates to a system for facilitating the functioning of a body organ, such as the assisting of the flow rate of a human heart.

In the past, there have been different techniques for assisting the functioning of human organs which have ceased to function properly due to disease or other reasons, such as injuries. For example, heart pacemakers have been employed to assist the proper functioning of the heart by supplying electrical impulses to it. The present day heart pacemakers are implanted in the chest cavity and are in the form of a pulse generator which is powered by a battery to supply impulses to electrodes positioned within the heart. The electrical pulses are supplied at a predetermined rate to stimulate the heart to beat at a desired rhythm. Such heart pacemakers have been highly successful for the treatment of heart disease where there is a lack of natural stimulation of the heart from the nervous system. While heart pacemakers have proven to be highly successful for many applications, it would be highly desirable to have a new and improved control system for assisting the operation of a body organ, such as a human heart, which has ceased to function properly as a result of heart disease and has a substantially reduced flow rate. In this regard, it would be highly desirable to have a control system which would assist the human heart in its pumping operation to increase substantially its flow rate.

Therefore, it is the principal object of the present invention to provide a new and improved control system for malfunctioning body organs, which control system can assist the malfunctioning body organ to function in a more nearly normal manner.

Briefly, the above and further objects of the present invention are realized by providing in a body organ control system having a pulse generator connected to a source of electrical power for generating a series of electrical timing pulses, an auxiliary pumping device attached to a portion of the body for compressing and releasing it alternatingly in response to the series of timing pulses. The pumping device includes a compressor which has an opening therein for receiving and at least partially surrounding the body organ. The compressor is movable periodically to reduce substantially and forcibly the cross-sectional area of the opening by a predetermined amount to squeeze the surrounded portion of the body organ to force body materials therefrom. The pumping device includes an electrical force producing device, such as an electrical motor or a pump, which responds to the timing pulses for applying force to the compressor to cause it to reduce substantially the cross-sectional area of the opening against the force of the body organ being squeezed upon the occurrence of each one of the pulses and for releasing the compressor to permit the body organ to expand rapidly back to its unstressed normal size and shape during the time intervals between the pulses. In this manner, for example, the flow rate of a diseased heart of a person can be increased substantially, whereby the physical activities of such a person can be increased substantially.

BRIEF DESCRIPTION OF THE DRAWINGS

The above-mentioned and other objects and features of this invention and the manner of attaining them will become apparent and the invention itself will be best understood by reference to the accompanying description of embodiments of the invention taken in conjunction with the accompanying drawings, wherein:

FIG. 1 is a cross-sectional plan view of the control system, which is constructed in accordance with the present invention and which is shown mounted in position within a chest cavity attached to a human heart for assisting its proper functioning;

FIG. 2 is a back elevational, cross-sectional view of the control apparatus of FIG. 1 taken substantially along the line 2—2 thereof illustrating the back side of the apparatus and the heart;

FIG. 3 is a symbolic block diagram of the electrical pulse generator of the control system shown in FIG. 2;

FIG. 4 is a horizontal cross-sectional plan view of another control system, which is constructed in accordance with the present invention and which is shown mounted on a human heart; and FIG. 5 is a fragmentary cross-sectional view of a portion of the control system of FIG. 4 taken substantially along the line 5—5 thereof.

DETAILED DESCRIPTION

Referring now to the drawings, and more particularly to FIGS. 1, 2 and 3 thereof, there is shown a control system 10, which is constructed in accordance with the present invention, and which is mounted on a front rib 12 within a rib cage generally indicated at 14 of a person having a malfunctioning heart 16, in order to assist its proper functioning by increasing substantially its flow rate. It will become apparent to those skilled in the art that the control system of the present invention may also be used for assisting the operation of other different body organs, such as the bladder, colon and others, to increase substantially their sluggish or non-existent operation.

The control system 10 generally comprises a compressor 18 which surrounds the lower portion of the heart 16 and is driven by an electric motor 20 mounted thereon as shown in FIG. 2 of the drawings. An electric cable 21 supplies a series of electrical timing pulses from a control unit 22 which may be implanted in the body in a similar manner as a heart pacemaker. The timing pulses are used to turn the motor 20 on and off alternatingly, whereby the electric motor in turn causes the compressor 18 to constrict and to release alternatingly the lower portion of the heart 16 to assist the pumping operation of the heart 16. The resulting operation is similar to the conventional manually-applied cardiac pulmonary resuscitation technique of assisting the operation of a heart, in that the lower portion of the heart, where the major pumping chambers are located, is alternatingly compressed and released by means of the system 10 of the present invention to increase the flow rate of the heart 16.

Considering now the compressor 18 in greater detail with reference to FIGS. 1 and 2 of the drawings, the compressor 18 includes an elongated support block 24 which is fastened to the front rib 12 opposite the lower portion of the heart 16 by means of a series of fastening devices 26 which may be in the form of U-shaped staples or the like which surround the rib 12 and are driven into the block 24. A flexible strap 28 extends around the back side of the lower portion of the heart 16 and with the front block 24 defines an opening 31 to receive the lower portion of the heart 16. As indicated in phantom lines shown in FIG. 1 of the drawings, when the motor 20 is energized, the effective length of the strap 28 is shortened so as to reduce forcibly the cross-sectional area of the opening 31 by a predetermined amount to squeeze the surrounded portion of the heart 16 to force blood therefrom.

The block 24 is composed of suitable soft stiff material which is somewhat resilient to engage the front side of the lower portion of the heart 16 as shown in FIG. 1 of the drawings. A complementary-shaped rear wall 33 of the block 24 engages and generally conforms to the shape of the front side of the bottom portion of the heart 16. A clevis end portion 35 projects rearwardly from one end of the block 24 and includes a pair of parallel, vertically spaced-apart projections 37 and 39 for supporting the motor 20 from the underside of the upper projection 37 as best seen in FIG. 2 of the drawings. A one-way clutch 41 couples drivingly the output of the motor 20 to a vertical shaft 42 which is journaled for rotation about its opposite end in the lower projection 39. A reel 43 is fixed to the shaft 42 between the projections 37 and 39 and is driven rotatably by the motor 20.

Considering now in greater detail the control unit 22, as shown in FIG. 3 of the drawings, the control unit 22 includes a pulse generator 45 which generates a square wave pulse train which, in turn, drives the electric motor 20 for turning it on and off periodically. A battery 47 powers the pulse generator 45. The pulse generator 45 and the battery 47 are encapsulated within a housing 22a as best seen in FIG. 2 of the drawings, the housing 22a being highly corrosion resistant.

In operation, the control unit 22 generates the series of electrical timing pulses and supplies them via the cable 21 to the electrical motor 20. In response to each one of these electrical timing pulses, the motor 20 is driven into operation to rotate drivingly the shaft 42 via the one-way clutch 41. As a result, the reel 43 is rotated about its axis in a counterclockwise direction as viewed in FIG. 1 of the drawings to coil one end 28A of the strap therein, the opposite end 28B of the strap 28 being fixed to the opposite end of the block 24 by any convenient means (not shown). Thus, as indicated by the phantom lines, the effective cross-sectional area of the opening 31 defined by the strap 28 and the block 24 effectively becomes smaller in size to exert a pressure on the lower portion of the heart 16 for forcing fluid therefrom, whereby the pumping operation of the heart 16 is substantially increased. In this regard, the strap 28 forces the back side of the lower portion of the heart 16 against the rear wall 33 of the block 24 for squeezing it. The flexible strap 28 grips frictionally the back side of the lower portion of the heart during the compression operation.

At the trailing edges of the timing pulses, the electrical motor 20 is deenergized to prevent further driving of the reel 43. Once the motor 20 is turned off, the heart 16 is permitted to expand according to its normal operation, since the one-way clutch 41 permits the reel 43 to rotate in a counterclockwise direction as viewed in FIG. 1 of the drawings and thus to permit the strap 28 to move from the phantom line position as shown in FIG. 1 of the drawings to the solid line position as indicated therein. In this regard, the end 28A of the strap moves out of the reel 43.

Once the heart has expanded back to its normal position, the next timing pulse energizes the motor 20, which in turn repeats the compressing cycle of operation.

It should be noted that the operation of the control unit 22 is an asynchronous operation to control the heart beat rhythm of the heart 16. However, it will become apparent to those skilled in the art that the control unit 22 can be made to operate synchronously in a similar manner that current heart pacemakers operate in a synchronous manner.

Referring now to FIGS. 4 and 5 of the drawings, there is shown a body organ control system 50, which is also constructed in accordance with the present invention and which is a hydraulically powered system for assisting the pumping operation of the heart 51.

The control system 50 generally comprises a tubular sleeve compressor 52 which surrounds the lower portion of the heart 51 and has an opening 53 therein for receiving snugly and grippingly the lower portion of the heart as indicated in FIG. 4 of the drawings. The hollow compressor 52 may be attached to the heart 51 by any suitable technique, such as securing it in place with sutures (not shown). A pump 54 discharges under pressure a suitable fluid, such as a saline solution, through a tube 56 to the compressor 52 for causing it to expand or inflate and thus to reduce forcibly the cross-sectional area of the opening 53, whereby the lower portion of the heart 51 is compressed to assist in its pumping operation by forcing fluids therefrom in a manner similar to the conventional manual cardiac pulmonary resuscitation technique.

The pump 54 alternatingly supplies and releases the pressure on the fluid supplied to the compressor 52. As a result, the lower portion of the heart 51 expands to help increase its flow rate. As in the case of the operation of the system 10, the heart is compressed to force fluids therefrom and alternatingly released to permit the heart to snap back resiliently to its normal unstressed condition to draw blood back therein.

An electrical control unit 58 supplies a series of electrical timing pulses via a cable 61 to the pump 54 in a similar manner as the control unit 22 supplies electrical impulses to the motor 20 for turning the compressor on and off alternatingly. A fluid reservoir 63 is connected in fluid communication with the pump 54 via a tube 65 so that, when fluid is forced out of the compressor 52 when the heart 51 expands back to its normal unstressed condition, fluid flows backwardly through the tube 56, the pump 54, the tube 65 and into the reservoir 63. The entire system 50 may thus be implanted in the chest cavity of the patient for continuous operation. Alternatively, the pump 54, the power supply control unit 58 and the reservoir 63 may be mounted externally of the chest cavity, and these units may be worn on the body, such as by attaching them to the belt of the user, whereby the tube 56 extends through a small opening (not shown) in the chest of the patient to the compressor 52.

Considering now the compressor 52 in greater detail with reference to FIGS. 4 and 5 of the drawings, the compressor 52 generally comprises a soft flexible molded sleeve unit 67 which fits snugly about the lower portion of the heart 51 and includes a series of equally spaced-apart cells or elongated chambers 69 which extend axially almost the entire axial length of the sleeve 67. The fluid flows into the cells 69 via a common passage 72 which extends circumferentially along the sleeve 67 and is disposed in fluid communication with the mid portions of the cells 69 as best seen in FIG. 5 of the drawings.

When fluid is forced into the common passage 72 via an opening 74 (FIG. 5) communicating with the tube 56, the fluid flows into each one of the cells 69 and causes it to expand. In this regard, each one of the cells 69 is normally unstressed and is generally elliptical in cross section as shown in solid lines in FIG. 4 of the drawings. When the cells 69 are inflated, they assume a generally circular cross-sectional shape as indicated in the phantom line showing in FIG. 4 of the drawings, thereby substantially reducing the cross-sectional area of the opening 53 in the sleeve 67.

While particular embodiments of the present invention have been disclosed, it is to be understood that various different modifications are possible and are contemplated within the true spirit and scope of the claims. For example, many different types and kinds of materials may be employed with the different components of the control system of the present invention. There is no intention therefore of limitations to the exact abstract or disclosure herein presented.

The embodiments of the invention in which an exclusive property or privilege is claimed are defined as follows:

1. In a body organ control system adapted to be totally implanted within a body for assisting the operation of a body organ and having an electrical power control unit connected for generating a series of electrical timing pulses at a desired frequency, the combination comprising: auxiliary pumping means adapted to be attached to and to surround a portion of the body organ for compressing and releasing it alternatingly in response to the series of timing pulses, means coupling electrically the output of the pulse generator to said auxiliary pumping means for enabling the pulse generator to supply the pulses to said pumping means for controlling it; said pumping means including compression means being adapted to surround a portion of the body organ and having an opening therein for receiving the body organ, said compression means reducing periodically substantially and forcibly the cross-sectional area of said opening by a predetermined amount to squeeze the surrounded portion of the body organ to force body materials therefrom, said pumping means including electrical force producing means responsive to said series of timing pulses for applying force to said compression means to cause it to reduce substantially the cross-sectional area of said opening against the force of the body organ being squeezed upon the occurrence of each one of said pulses and for releasing said compression means to permit the body organ to expand rapidly back to its unstressed normal size and shape during the time intervals between said pulses, said compression means to be implanted totally within the body and including support means to be fixed directly to and to engage directly another internal body portion of the body near said body organ, said support means having a rear wall for engaging directly the body organ, fastening means for attaching fixedly said support means directly to and in engagement with said another internal body portion disposed within the body for anchoring purposes, elongated strap means connected at its ends to said support means independent of said fastening means to cooperate with said rear wall of said support means to define said opening for engaging directly and for squeezing and compressing the body organ, and said force producing means for applying said force to said strap means to squeeze said surrounded portion of the body organ against said support means and alternatingly to release said strap means.

2. In a body organ control system, the combination according to claim 1, wherein said electrical force producing means includes an electric motor.

3. In a body organ control system, the combination according to claim 1, wherein said force producing means pulling on said strap means away from a fixed portion thereof to tighten said strap means about the body organ during the compressing of it.

4. In a body organ control system, the combination according to claim 3, wherein said compression means further includes a reel mounted on said fixed portion of said strap means and connected to said another portion of said strap means, said force producing means being drivingly connected to said reel to effectively shorten said strap means when said force producing means rotates said reel for winding said strap means thereabout.

5. In a body organ control system, the combination according to claim 4, wherein said support means includes an elongated support block, and said strap means being a flexible strap fixed at one of its ends to one end of the support block and for extending along the opposite side of the body organ and being coupled at its opposite end to said reel, said reel being mounted on the opposite end of said support block.

6. In a body organ control having an electrical power control unit connected for generating a series of electrical timing pulses at a desired frequency corresponding to a desired pulse rate for the body organ, the combination comprising: auxiliary pumping means adapted to be attached to a portion of the body organ for compressing and releasing it alternatingly in response to the series of timing pulses, means coupling electrically the output of the pulse generator to said auxiliary pumping means for enabling the pulse generator to supply the pulses to said pumping means for controlling it; said pumping means including compression means being adapted to surround a portion of the body organ and having an opening therein for receiving the body organ, said compression means reducing periodically substantially and forcibly the cross-sectional area of said opening by a predetermined amount to squeeze the surrounded portion of the body organ to force body materials therefrom, said pumping means including electrical force producing means responsive to said series of timing pulses for applying force to said compression means to cause it to reduce substantially the cross-sectional area of said opening against the force of the body organ being squeezed upon the occurrence of each one of said pulses and for releasing said compression means to permit the body organ to expand rapidly back to its unstressed normal size and shape during the time intervals between said pulses, said compression means includes strap means extending around the portion of the body organ, at least a portion of said strap means being adapted to be fixed to another portion of the body, said force producing means pulling on another portion of said strap means away from the fixed portion thereof to tighten said strap means about the body organ during the compressing of it, said compression means further includes a reel mounted on said fixed portion of said strap means and connected to said another portion of said strap means, said force producing means being drivingly connected to said reel to effectively shorten said strap means when said force producing means rotates said reel for winding said strap means thereabout, said strap means includes an elongated support block and a flexible strap fixed at one of its ends to one end of the support block and extending along the opposite side of the body organ and being coupled at its opposite end to said reel, said reel being mounted on the opposite end of said support block, said opposite end of said support block has a rearwardly extending clevis end portion having mounted thereon said reel, said force producing means mounted on said clevis end, a one-way clutch means drivingly coupling said force producing means to said reel so that said force producing means drives said reel to tighten said strap about said body organ in response to the presence of said timing pulses, said reel rotating in a reverse direction during the absence of said pulses when said body organ expands back to its unstressed condition as permitted by said one-way clutch means.

7. In a body organ control system, the combination according to claim 6, said elongated support block having a complementally-shaped rear wall for engaging the body organ, said elongated support block being composed of soft, slightly flexible, resilient material, said strap being composed of flexible material.

8. In a body organ control system, the combination according to claim 1, said electrical power control unit including a pulse generator for generating the timing pulses, and a source of electrical power for energizing said pulse generator.

9. A body organ control system for assisting the operation of a body organ of a body, comprising: an electrical power control unit connected for generating a series of electrical timing pulses at a desired frequency, auxiliary pumping means adapted to be attached to and to surround a portion of the body organ for compressing and releasing it alternatingly in response to the series of timing pulses, means coupling electrically the output of the pulse generator to said auxiliary pumping means for enabling the pulse generator to supply the pulses to said pumping means for controlling it; said pumping means including compression means being adapted to surround a portion of the body organ and having an opening therein for receiving the body organ, said compression means reducing periodically substantially and forcibly the cross-sectional area of said opening by a predetermined amount to squeeze the surrounded portion of the body organ to force body materials therefrom, said pumping means including electrical force producing means responsive to said series of timing pulses for applying force to said compression means to cause it to reduce substantially the cross-sectional area of said opening against the force of the body organ being squeezed upon the occurrence of each one of said pulses and for releasing said compression means to permit the body organ to expand rapidly back to its unstressed normal size and shape during the time intervals between said pulses, said compression means to be implanted totally within the body and including support means to be fixed directly to and to engage directly another internal body portion of the body near said body organ, said support means having a rear wall for engaging directly the body organ, fastening means for attaching fixedly said support means directly to and in engagement with said another internal body portion disposed within the body for anchoring purposes, elongated strap means connected at its ends to said support means independent of said fastening means to cooperate with said rear wall of said support means to define said opening for engaging directly and for squeezing and compressing the body organ, and said force producing means for applying said force to said strap means to squeeze said surrounded portion of the body organ against said support means and alternatingly to release said strap means.

* * * * *